United States Patent [19]
Lathe et al.

[11] Patent Number: 6,024,953
[45] Date of Patent: Feb. 15, 2000

[54] VACCINE AGAINST RABIES AND PROCESS FOR PREPARATION THEREOF

[75] Inventors: Richard Lathe; Marie-Paule Kieny; Robert Drillien, all of Strasbourg; Jean-Pierre Lecocq, Reichsteet, all of France

[73] Assignee: Transgene S.A., Strasbourg, France

[21] Appl. No.: 08/231,457

[22] Filed: Apr. 21, 1994

Related U.S. Application Data

[63] Continuation of application No. 08/038,052, Mar. 29, 1993, abandoned, which is a continuation of application No. 07/759,138, Sep. 11, 1991, abandoned, which is a continuation of application No. 07/378,801, Jul. 11, 1989, abandoned, which is a continuation of application No. 06/829,144, Dec. 24, 1985, abandoned.

[30] Foreign Application Priority Data

Apr. 25, 1984 [FR] France .................................. 84 06499
Apr. 24, 1985 [WO] WIPO ..................... PCT/FR85/00096

[51] Int. Cl.⁷ ............................. A61K 48/00; C12N 15/86
[52] U.S. Cl. ........................................ 424/93.2; 435/320.1
[58] Field of Search .............................. 435/235.1, 172.3, 435/320.1; 424/93 A, 93.2, 93.6; 514/44

[56] References Cited

U.S. PATENT DOCUMENTS

| | | | |
|---|---|---|---|
| 4,393,201 | 7/1983 | Curtis | 536/23.72 |
| 4,722,848 | 2/1988 | Paoletti et al. | 424/199.1 |

FOREIGN PATENT DOCUMENTS

| | | |
|---|---|---|
| 0083286 | 6/1983 | European Pat. Off. . |
| 2526661 | 5/1982 | France . |
| 2552776 | 10/1983 | France . |
| 2562090 | 3/1984 | France . |

OTHER PUBLICATIONS

New Vaccine and Initiative Mean End of Rabies in Sight for Europe?, Nature, vol. 336, 1 Dec.
The Wistar Institute Announces New Recombinant Rabies Vaccine Trials in Western Europe, Plans for U.S. Trials, Wistar News Release, May 3, 1988, The Wistar Institute.
Rabies Vaccine Ready for Testing, International Herald Tribune, Thursday, May 19, 198.
U.S. Test Sought of Vaccine, News/Sun–Sentinel, Thursday, May 5, 1988.
Recombinant DNA Research and Wildlife Studies Focus on Reducing the Spread of Rabies, Research Resources Report, vol. X, No. 4, Apr. 1986.
Verma (1977), Biochim. Biophys. Acta 473: 1–38.
Paoletti et al, *Proc. Natl. Acad. Sci. USA*, vol. 81, pp. 193–197 (1984).
Panicali et al, *Proc. Natl. Acad. Sci USA*, vol. 80, pp. 5364–5368, (1983).
Smith et al, *Proc. Natl. Acad Sci USA*, vol. 80, pp. 7155–7159, (1983).
Dietzschold et al, *Journal of Virology*, vol. 44, pp. 595–602, (1982).
Nature, vol. 312, Nov. 8, 1984, M.P.Kieny et al: "Expression of rabies virus glycoprotein from a recombinant vaccinia virus", pp. 163–166, see the whole article.
Proceedings of the National Academy of Sciences, vol. 81, Nov. 1984 (US) T.J.Wiktor et al: "Protection from rabies by a vaccinia virus recombinant containing the rabies virus glycoprotein gene", pp. 7194–7198, see the whole article.

*Primary Examiner*—Nancy Degen
*Assistant Examiner*—Robert Schwartzman
*Attorney, Agent, or Firm*—Burns, Doane, Swecker & Mathis, L.L.P.

[57] ABSTRACT

The present invention relates to a vaccinia virus, characterised in that it contains all or part of a DNA sequence (I) coding for an antigenic glycoprotein of rabies.

9 Claims, 14 Drawing Sheets

```
                                                                    -19
Pstl
     1                                               22                             ATG GTT CCT CAG GCT CTC CTG
     CTG CAG GGG GGG GGG GGA GGA AAG                                                 Aet Val Pro Glu Ala Leu Leu
                                                                                          1
     49                                      71
     TTT GTA CCC CTT CTG GTT TTT CCA TTG TGT TTT GGG AAA TTC CCT ATT
     Phe Val Pro Leu Leu Val Phe Pro Leu Cys Phe Gly Lus Phe Pro ILe
                             HindIII                  HgiIII
     98                                     120
     TAC ACG ATA CTA GAC CTT ADA CTT GGT CCC TGG AGC CCG ATT GAC ATA CAT
     Tyr Thr Ile Leu Asr Leu Lys Leu Gly Pro Trr Ser Pro ILe Asp ILe His
                    PvuII
     147                                   169
     CAC CTC ACT TGC CCA AAC AAT TTG GLA GTG GAG GAC GAA GGA TAC ACC
     His Leu Ser Cyo Pro Asa Asa Leu Val Gly Asp Glu Gly Cys Thr 196                                   218
     AAC CTG TCA GGG TTC TCC TAC ATG GAA CTT AAA GTT GGA TAC ATC TTA
     Asa Leu Ser Gly Phe Ser Tyr Met Gly Leu Lys Val Gly Tyr ile Leu
```

FIG. 1A

| 245 | GCC | ATA | AAA | ATG | AAC | GGG | TTC | ACT | TGC | ACA | GGC | GTT | GTG | ACG | GAG | GCT |
| | Ala | Ile | Lys | Het | Asp | Gly | Phe | Thr | Lys | Thr | Gly | Val | Val | Thr | Gly | Ala |
| | | | | | | | 266 | | | | | | | | | |

| 293 | GAA | ACC | TAC | ACT | AAC | TTC | GTT | GGT | TAT | GTC | ACA | CCA | ACC | ACG | TTC | AAA | AGA |
| | Glu | Thr | Tyr | Thr | Asp | Phe | Val | Gly | Tyr | Val | Thr | Pro | Thr | Thr | Phe | Lys | Arg |
| | | | | | | | 314 | | | AvaIII | | | | | | | |

| 341 | AAG | CAT | TTC | CGC | CCA | ACA | CCA | GAL | GCG | TGT | AGA | GCC | GCG | TAC | AAC | TGG |
| | Lys | His | Phe | Arg | Pro | Thr | Pro | Asp | Ala | Cys | Arg | Ala | Ala | Tyr | Asa | Trr |
| | | | HpaII/BstEII | | | | 362 | | | | | | | | | |

| 389 | AAG | ATG | GCC | AAC | GAC | CCC | AGA | TAT | GAA | GAG | TCT | CTA | CAC | AAT | CCG | TAC |
| | Lys | Hel | Ala | Gly | Asp | Pro | Arg | Tyr | Glu | Glu | Ser | Leu | His | Asa | Pro | Tyr |
| | | | | | | AsuII | 410 | | | | | | | | | |

| 437 | CCT | GAC | TAC | CGC | TGG | CTT | CGG | ACT | GTA | AAA | ACC | ACC | AAG | GAG | TCT | CTC |
| | Pro | Asp | Tyr | Arg | Tre | Leu | Arg | Thr | Val | Lys | Thr | Thr | Lys | Gly | Ser | Leu |
| | | | | | | | 458 | | | | | | | | | |

FIG. 1B

485
GTT ATC ATA TCT CCA AGT GTA GCA GAT TTG GAC CCA TAT GAC AGA TCC
Val Ile Ile Ser Pro Ser Val Ala Asp Leu Asp Pro Tyr Asp Arg Ser
            XhoI AvaI

533
CTT CAC TCG AGG BTC TTC CCT AGC GGG AAG TGC TCA GGA GTA GCG GTG
Leu His Ser Arg Val Phe Pro Ser Gly Lys Cys Ser Gly Val Ala Val
                                                              AvaI

581
TCT TCT ACC TAC TGC TCC ACT AAC CAC GAT TAC ACC ATT TGG ATG CCC
Ser Ser Thr Tyr Cyg Ser Thr Asa His Asp Tyr Thr ILe Trr Het Pro

629
GAG AAT CCG AGA CTA GGG ATG TCT TGT GAC ATT TTT ACC AAT AGT AGT
Glu Asa Pro Arg Leu Gly Hat Ser Cys Asp ILe Phe Thr Asa Ser Arg

677
GGG AAG AGA GCA TCC AAA GGG AGT GAG ACT TGC GGC TTT GTA GAT GAA
Gly Lys Arg Ala Ser Lys Gly Ser Gly Thr Cys Gly Phe Val Asp Gly

FIG. 1C

```
                                            StuIHaeI                    AhaIII                                    SphI                              NruI                                    BgaI
725  AGA  GGC  CTA  TAT  AAG  TCT  TTA  AAA  GGA  GCA  AAA  CTC  AAG  TTA  TGT
     Arg  Gly  Leu  Tyr  Lys  Ser  Leu  Lys  Lys  Ala  Lys  Leu  Lys  Leu  Cys
                                        746
773  GGA  GTT  CTA  GGA  CTT  AGA  CTT  ATG  GAT  GGA  ACA  TGG  GTC  GCG  ATG  CAA
     Gly  Val  Leu  Gly  Leu  Arg  Leu  Met  Asp  Gly  Thr  Gre  Val  Als  Met  Gln
                                        794
821  ACA  TCA  AAT  GAA  ACC  AAA  TGG  TGC  CCT  CCC  GAT  CAG  TTG  GTG  AAC  CTG
     Thr  Ser  Asa  Gly  The  Lys  Trr  Cws  Pro  Pro  Asp  Gln  Leu  Val  Asp  Leu
                                        842
869  CAC  GAC  TTT  CGC  TCA  GAC  GAA  ATT  GAG  CAC  CTT  GTT  GTA  GAG  GAG  TTG
     His  Asp  Phe  Arg  Ser  Asp  Glu  Ile  Glu  His  Leu  Val  Val  Glu  Glu  Leu
                                        890
917  GTC  AGG  AAG  AGA  GAG  GAG  TGT  CTG  GAT  GCA  CTA  GAG  TCC  ATC  ATG  ACA
     Val  Arg  Lws  Arg  Glu  Glu  Cys  Leu  Asp  Ala  Leu  Glu  Gly  Ser  ILe  Met  Thr
                                        938
```

FIG. 1D

```
                                              Acyl
                                               986
     ACC AAG TCA GTG AGT TTL AGA CGT CTC AGT CAT TTA AGA AAA CCT GTC
965  Thr Lys Ser Val Ser Phe Arg Arg Leu Ser His Leu Arg Lys Leu Val 1034
     CCT GGG TTT GGG AAA GCA TAT ACC ATA TTC AAC AAG AGC TTG ATG GAA
1013 Pro Gly Phe Gly Lys Ala Tyr Thr Ile Phe Asa Lys Thr Leu Met Gly 1082
     GCC GAT GCT CAC TAC AAG TCA GTC AGA ACT TGG AAT GAG ATC CTC CCT
1061 Ala Asp Ala His Tyr Lys Ser Val Arg Thr Trr Asp Glu Ile Leu Pro 1130
     TCA AAA GGG TGT TTA AGA GGG GGG AGG TGT CAT CCT CAT GTG AAC
1109 Ser Lys Gly Cys Leu Arg Val Gly Gly Arg Cys His Pro His Val Asn 1178
     GGG GTG TTT TTC AAT GGT ATA ATA TTA GGA CCT GAC GGC AAT GTC TTA
1157 Gly Val Phe Phe Asp Gly Ile Ile Leu Gly Pro Asp Gly Asn Val Leu
```

FIG. 1E

```
1205
     ACT CCA GAG ATG CAA TCA TCC CTC CAG CAA CAT ATG GAG TTG TTG
     Ile Pro Gly Met Glu Ser Ser Leu Gln Gln His Met Glu Leu Leu
                                    1226
1253
     GAA TCC TCG GTT ATC CCC CTT GTG CAC CCC CTG GCA GAC CCG TCT ACC
     Glu Ser Ser Val Ile Pro Leu Val His Pro Leu Ala Asp Pro Ser Thr
                                    1274                          AccI
1301
     GTT TTC AAG GAC GGT GAC GAG GCT GAG GAT TTT GTT GAA GTT CAC CTT
     Val Phe Lys Asp Gly Asp Glu Ala Glu Asp Phe Val Glu Val His Leu
                                    1322                HindII
1349
     CCC GAT GTG CAC AAT CAG GTC TCA GGA GTT GAC TTG GGT CTC CCG AAC
     Pro Asp Val His Asn Gln Val Ser Gly Val Asp Leu Gly Leu Pro Asn
                                    1370             ApaI HgI III
1397
     TGG GGG AAG TAT GTA TTA CTG AGT GCA GGG GCC CTG ACT GCC TTG ATG
     Trr Gly Lys Tyr Val Leu Leu Ser Ala Gly Ala Leu Thr Ala Leu Met
                                    1418
```

FIG. 1F

```
1445 TTG ATA ATT TTC CTG ATG ACA TGT TGT AGA AGA GTC AAT CGA TCA GAA
    Leu Ile Ile Phe Leu Met Thr Cys Cys Arg Arg Val Asp Arg Ser Glu
                        1466

1493 CCT ACG CAA CAC AAT CTC AGA GGG ACA GGG AGG GAG GTG TCA GTC ACT
    Pro Thr Gln His Asn Leu Arg Gly Thr Gly Arg Gly Val Ser Val Thr
                1514

1541 CCC CAA AGC GGG AAG ATC ATA TCT TCA TGG GAA TCA CAC AAG AGT GGC
    Pro Gln Ser Gly Lys Ile Ile Ser Ser Trr Gly Ser His Lys Ser Gly
                    505     1562

1589 GGT GAG ACC ABA CTG TGA GGA CTG GCC GTC CTT TCA ACG ATC CAA GTC
    Gly Glu Thr Arg Leu ***
                1610

1637 CTG AAG ATC ACC TCC CCT TGG GGG GTT CTT TTT AAA AAA AAA AAA AAA
                                              Pstl
                1658

1685 AAA AAA AAA ACC CCC CCC CCC CCC CCC CTG CAG
                1706
```

FIG. 1G

```
                                    Met Val Pro Gln Ala
A  ———G₂₃——— AGGAAAGATGGTT CCT CAG GCT ———
                                        ↑MstII

B  5'GATCTAATATGGTTCC 3'
   3'ATTATACCAAGGAGT 5'

C  ———AGATCTAATATGGTT CCT CAG GCT ———
        BglII              MstII

———CTGCAG———
     PstI plg 155
```

FIG. 2

```
EcoRI    BglII                              Met  ---------  TyrThrIleLEUAspLysLeu ---  HindIII
GAATTC--- AGATCT--- ATG ---------  TACACGATACTAGACAAGCTT ---

*  *
                          5' - TACACGATCCCAGACAAGC - 3'
                                      * * * *

EcoRI    BglII                              Met  ---------  TyrThrIlePROAspLysLeu ---  HindIII
GAATTC--- AGATCT--- ATG ---------  TACACGATCCCAGACAAGCTT ---
```

FIG. 3

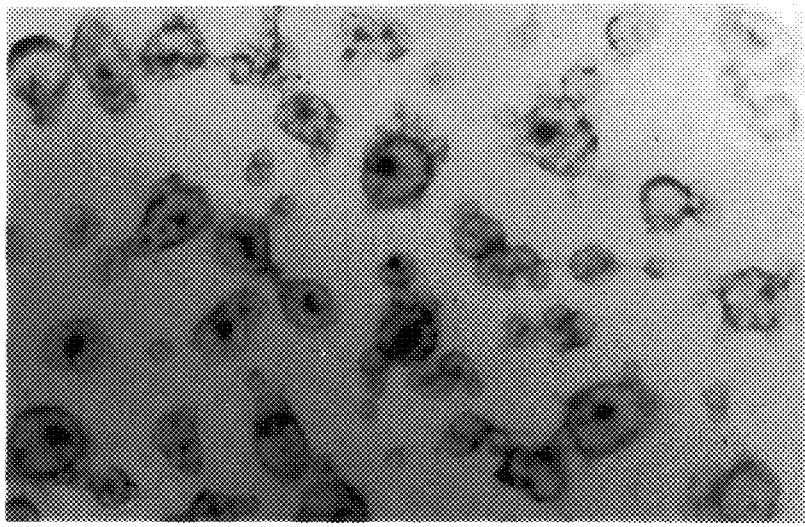
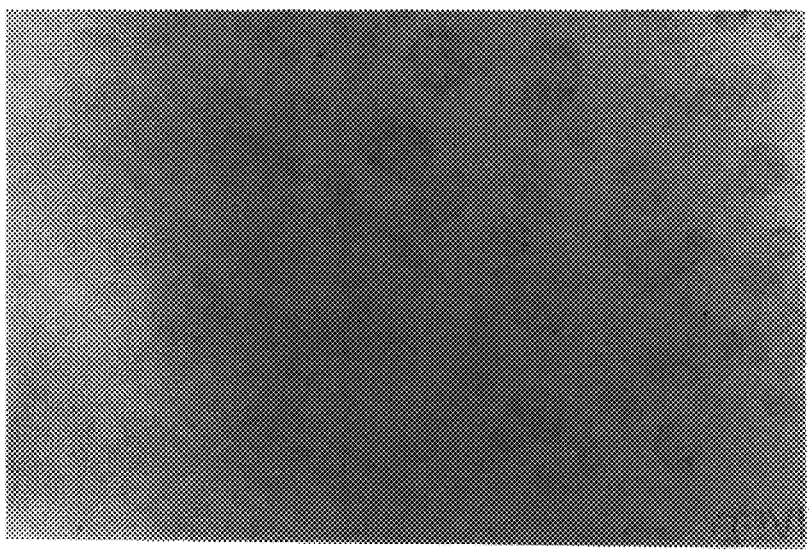
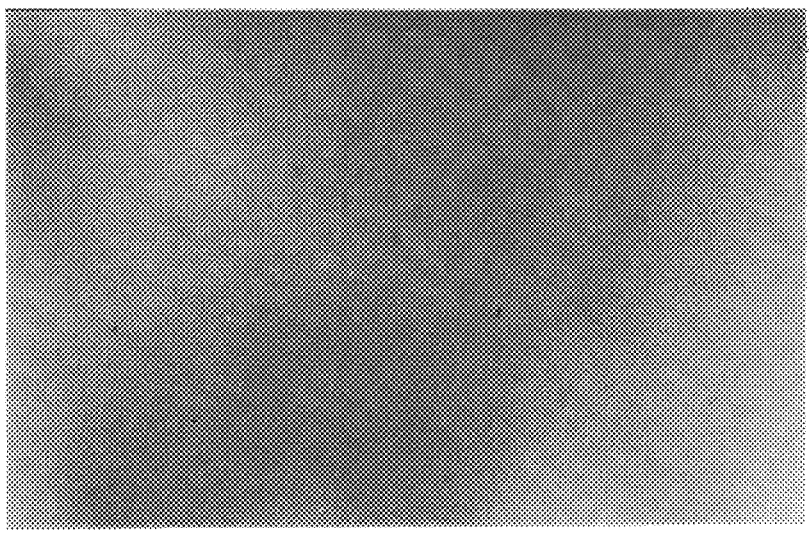
FIG. 8

VACCINE AGAINST RABIES AND PROCESS FOR PREPARATION THEREOF

This application is a continuation of application Ser. No. 08/038,052, filed Mar. 29, 1993, abandoned; which is a continuation of application Ser. No. 07/759,138, filed Sep. 11, 1991, abandoned, which is a continuation of application Ser. No. 07/378,801, filed Jul. 11, 1989, abandoned, and which is a continuation of application Ser. No. 06/829,144, filed Dec. 24, 1995, also abandoned.

Rabies is a very ancient disease, but it has not hitherto been possible to effect complete control thereof. Although there are effective vaccines against rabies, such vaccines are too costly to be usable preventively. More-over a very important reservoir of rabies virus exists in wild animals, and for this reason only island countries such as Great Britain and Japan have managed to eradicate this scurge.

The causative agent of this disease is a rhabdovirus. The transmission of rabies generally involves a receptor individual being bitten by an infected animal; the change in behaviour associated with chronic infection has an important role in the etiology of the disease.

In man, infection is followed by a dormancy period during which the virus travels through the nervous system to the brain. At the beginning, this disease can be treated effectively by intensive vaccination; however, when the behaviour symptoms appear, death is almost inevitable.

The virus contains 5 viral proteins, only one of which, the glycoprotein (G., haemagglutinin), passes through the lipid bilayer sheathing the virus. Thus, the glycoprotein is the only viral component capable of reacting with antibodies which neutralise the virus, and also of inducing production thereof. Anilionis et al. (1981) have described the isolation of a coding sequence corresponding to the messenger RNA of the glycoprotein of rabies strain ERA, and Lathe et al. (1984) have described the expression of this sequence in a bacterium.

Similar results have been reported by Yelverton et al. (1983) using a second rabies strain, CVS.

However, it has not yet been possible to carry out effective immunisation against rabies virus using the material synthesised by the bacteria.

Preliminary results suggest that post-translational modifications and/or presentation of the glycoprotein are important parameters in the use of this antigen to confer protection against rabies virus.

The present invention describes the expression of a sequence coding for the rabies glycoprotein in an environment such that correct modification and presentation of the primary translation products can take place.

Two groups have recently demonstrated the use of living recombinants of vaccinia virus to express the influenza or hepatitis B antigen for immunisation against these diseases (Smith et al., 1983; Panicali et al., 1983).

The expression of a sequence coding for an exogenous protein in vaccinia virus (VV) necessarily involves two stages:

1) The coding sequence must be aligned with a VV promoter and be inserted in a non-essential segment of the VV DNA cloned in a suitable bacterial plasmid;
2) The VV DNA sequences located on either side should permit homologous recombinations to take place in vivo in the plasmid and the viral genome. A reciprocal double recombination leads to a transfer of the plasmid DNA insert into the viral genome in which it is propagated and expressed (Panicali and Paoletti, 1982; Mackett et al., 1982; Smith et al., 1983; Panicali et al., 1983).

DESCRIPTION OF THE DRAWINGS

FIGS. 1A–1G show the nucleotide, and corresponding amino acid, sequence for rabies glycoprotein.

FIGS. 2A–2C show in A the plasmid pTG150, in B a partial duplex of hybridized oligonucleotides and plasmid pTG150, and in C the plasmid pTG155.

FIG. 3 shows pTG155 and the mutant site at the 8th amino acid.

FIGS. 8A–C show the fluorescent labeling with antibodies to glycoprotein of (A) cells infected with VVgRAB-26D3, (B) cells infected with non-recombinant virus and (C) unifected cells.

Figure 4:
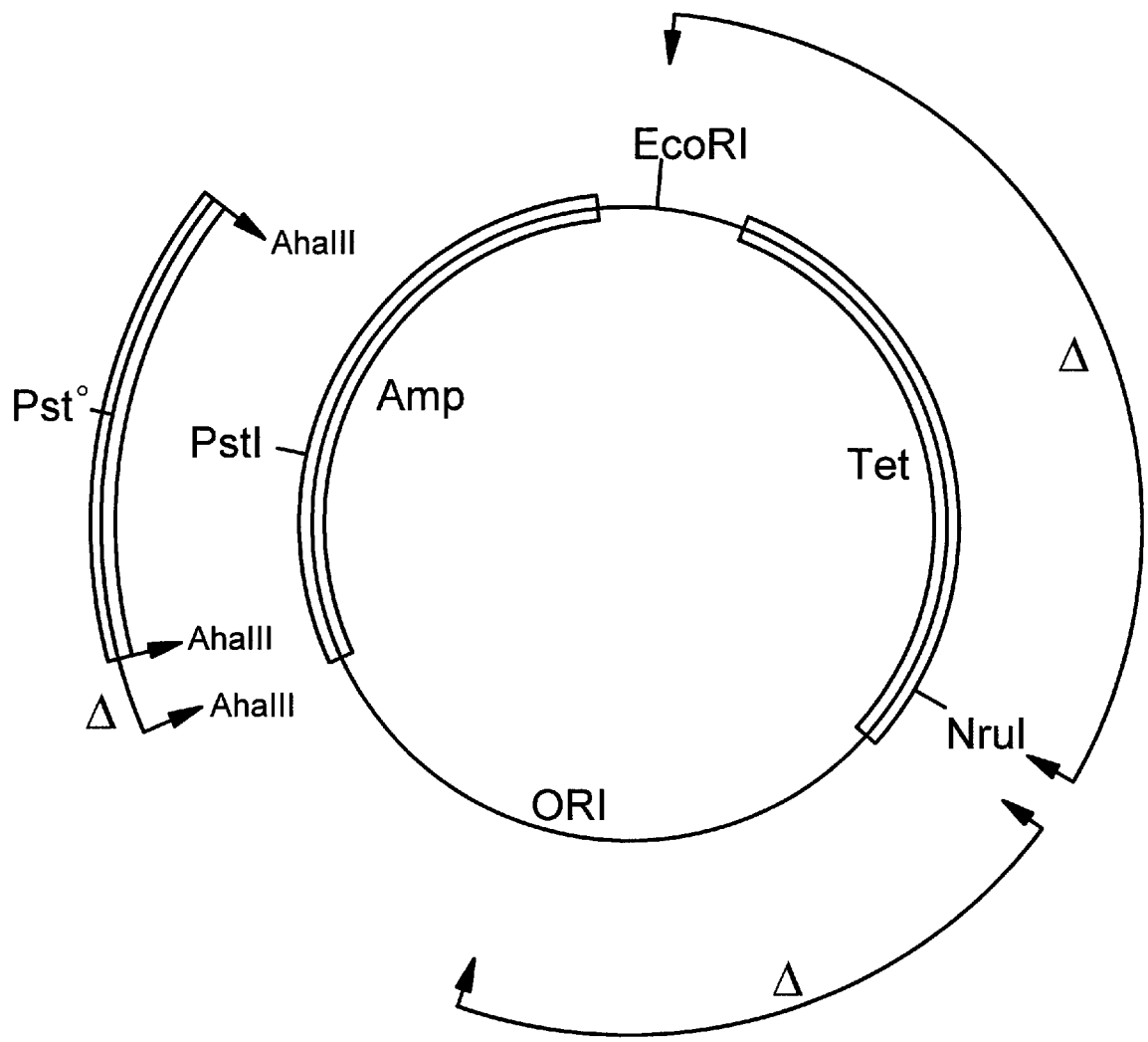
FIG. 4 shows the construction of mini-plasmid pTG1H.

The present invention relates to a vaccinia virus characterised in that it contains all or part of a DNA sequence coding for an anti genic glycoprotein of rabies, hereinafter called DNA sequence (I). "Vaccinia virus" is understood to denote all or part of a virus of the Pox virus genus, in particular the sub-genus Vaccinia, which incorporates, in addition to vaccinia itself, other viruses such as "Cowpox".

"Antigenic glycoprotein of rabies" is understood to denote a glycoprotein which, in vitro but preferably in vivo, has immunogenic characteristics identical or closely related to those of true rabies glycoprotein, that is to say the glycoprotein of the wild type virus.

Although it is preferred to use for the DNA sequence (I) the DNA sequence coding for the complete mature protein, it is possible to use only a portion of this DNA sequence, or such a sequence bearing point mutations but which lead to products having quasi-identical activities. This virus will preferably contain the combination of elements providing for the expression of the said glycoprotein, in particular a vaccinia gene promoter such as the 7.5 K gene promoter referred to as P 7.5 K, which will be placed up-stream of the DNA sequence (I).

This promoter/DNA sequence (I) combination will be inserted into a vaccinia virus gene, for example the TK gene, and this will provide a possible means of selection, as will be explained below.

The hybrid virus thus obtained can be used as such, live or inactivated by chemical or physical treatment, as a vaccinating agent, or can alternatively be used to infect a cell culture from which the antigenic glycoprotein may be extracted from the ground cell preparation by known techniques.

To reduce to a minimum the risks of accidents when vaccinating with a live virus, it is also possible to envisage using a temperature-sensitive mutant of vaccinia (F. Keller et al., 1978 and F. Keller and R. Drillien, 1980).

This type of ts mutation can exist on the vaccine vector itself or alternatively can be introduced by mutation in the recombinant viruses according to the invention. In particular, it is possible to introduce different temperature-sensitivities in the recombinant virus in order to maintain the phenotype even in cases of partial reversion.

Furthermore, it is possible to provide for the use of a mutant vaccinia virus having a host specificity, which does not grow, or grows to only a small extent, on human cells, and the pathogenicity of which is still weaker than that of vaccinia.

The present invention relates, in addition, to vaccines intended for treating or preventing rabies, characterised in that they contain a hybrid virus according to the invention, or a glycoprotein, obtained by carrying out the above process.

The invention also relates to the antisera obtained from animals immunised with the vaccines according to the invention.

With these vaccines, the methods of administration can be varied, and in particular the intradermal or oral route can be used. These vaccines can be administered with known pharmaceutical carriers, and contain in addition adjuvants which enable their vaccinating power to be increased.

The examples below are designed to demonstrate other characteristics and advantages of the present invention.

Figure 5:
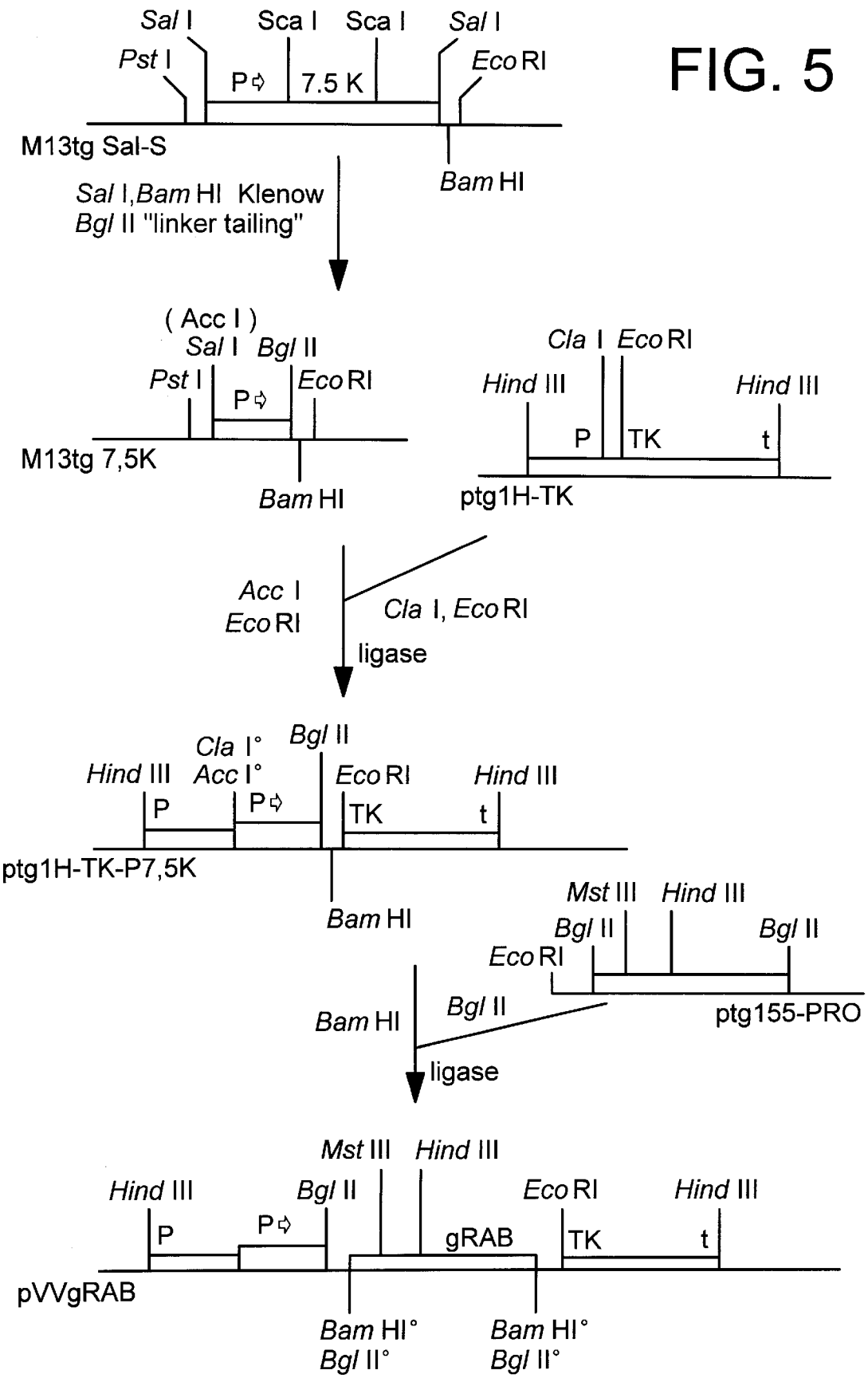
FIG. 5 shows the generation of pTG1H-TK-P705K.
Figure 6:
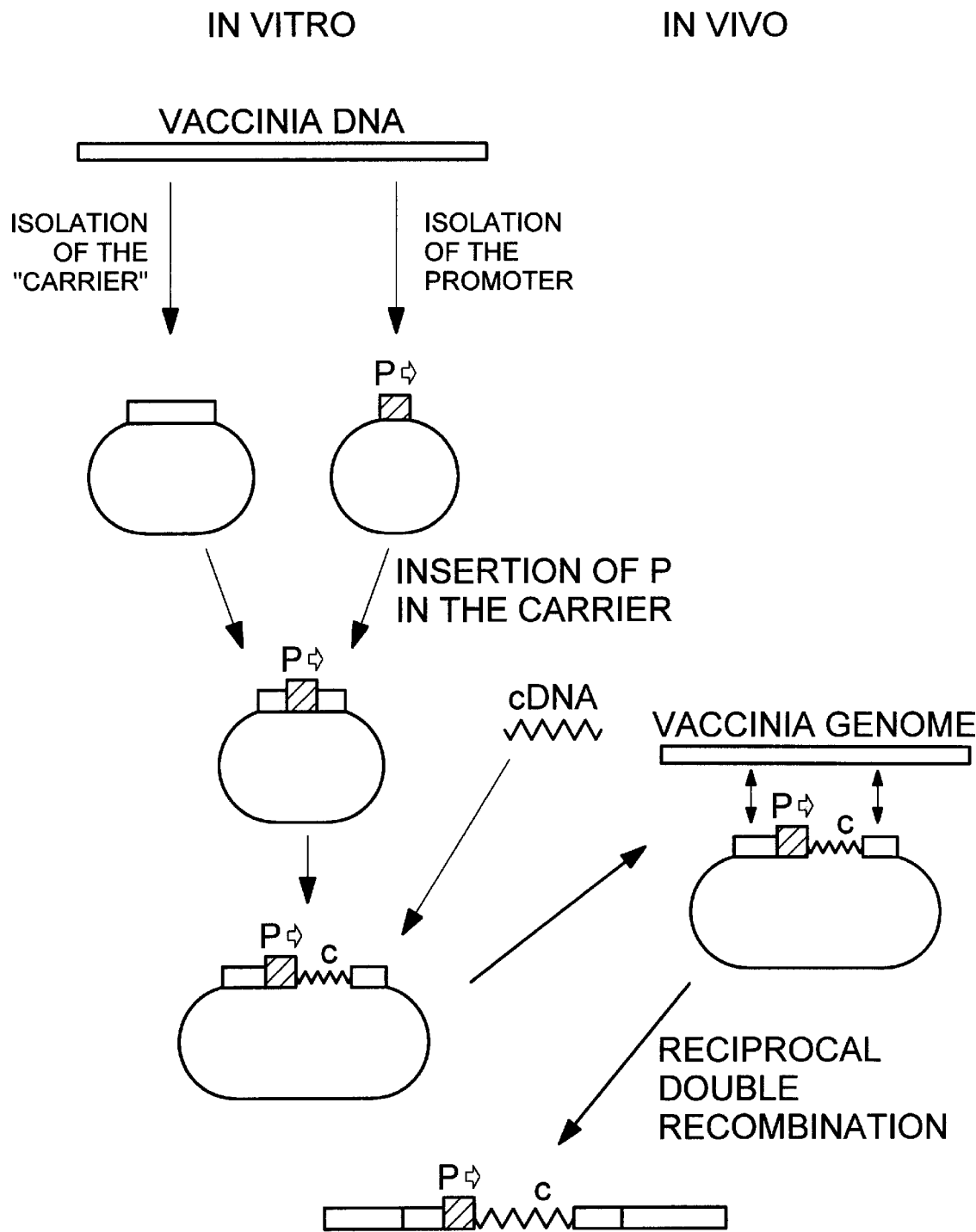
FIG. 6 shows the cloning of a plasmid in vaccinia virus.

The preparation of the virus according to the invention includes, in particular, the following stages:

1) Restructuring of one end of rabies cDNA, shown schematically in FIG. 1, by the process shown schematically in FIG. 2, to obtain pTG155;
2) Mutation of one of the sequences of this cDNA in order to re-establish proline at the 8th amino acid in the glycoprotein, FIG. 3, to obtain pTG155-pro;
3) Synthesis of a mini-plasmid pTG1H from pBR322 (FIG. 4);
4) Insertion in this mini-plasmid of the Hin-J fragment bearing the TK gene of VV;
5) Insertion in the TK gene of the 7.5 K protein promoter (FIG. 5);
6) Insertion under the P 7.5 K promoter of the rabies gene carried by pTG155-pro (FIG. 5);
7) Cloning of the essential elements of this latter plasmid in vaccinia virus (FIG. 6).

The examples which follow illustrate the properties of the different components obtained.

The different materials used are identified in the examples.

Except where otherwise stated, the enzymes are used under the conditions recommended by the manufacturer and the techniques carried out are known to the specialist.

The amino acid sequences and nucleotide sequences shown in the figures are not listed in the body of the description to avoid encumbering it, but they constitute an integral part thereof.

Restructuring of the Rabies Glycoprotein cDNA

The sequence coding for the rabies glycoprotein, published by Anitionis et al. and shown in FIG. 1, contains elements which can interfere with its translation and its expression as an antigen.

The rabies glycoprotein cDNA from plasmid pRG described by Anilionis et al. (1981), which is carried on a BglII-BglII fragment by different plasmids such as pTG147, pTG171 and pTG150, has already been described in French Patent No. 83/15716.

In the first place, the ATG corresponding to the initiation codon for the mature message is situated immediately adjacent to a polyG sequence introduced by the cDNA cloning procedure. This sequence is capable of causing instability during the recombination in vivo between the G/C elements at each of the ends of the cDNA and can in addition interfere with the translation of the message.

Then, the glycoprotein cDNA sequences do not correspond exactly with the sequence coding for the N-terminal portion of the mature glycoprotein. For this reason it was decided to remove these two obstacles before carrying out the cloning of the corresponding sequence.

Kozak (1981, 1983) has shown that the initiation codons of translation in eucaryotes are normally present in a sequence which can be represented in the following manner: A X X ATG (A or G), and alterations in this sequence can lead to reductions in translation. Although the importance of these end nucleotides is not fully established, it appears to be preferable to remove the adjacent G/C sequence and retain the essence of the consensus sequence mentioned above. Furthermore, it is necessary to provide for a BglII recognition sequence upstream, so as to facilitate subsequent manipulation.

By restructuring the 5' end of the cDNA, as shown in FIG. 2, advantage has been taken of a single MstII site which overlaps the codons coding for amino acids 2, 3 and 4 of the primary translation product.

In plasmid pTG150, the rabies glycoprotein cDNA of Anilionis has been inserted, by using PstI-BglII adaptor oligonucleotides (Lathe et al. 1982), in a single BglII site inserted in the HindIII site of plasmid pBR327 (Soberon et al., 1980).

This plasmid, represented by A in FIG. 2, was partially digested with BGlII and completely digested with MstII, and the appropriate linear fragments were isolated by gel electrophoresis on agarose having a low gellification temperature. The oligonucleotides (5'-dGATCTAAT-ATGGTTCC-3') and (5'-dTGAGGAACCATATTA-3') were synthesised according to a technique described earlier (Kohli et al., 1982). The oligonucleotides are hybridised to give a partial duplex (B in FIG. 2) and inserted between the BglII and MstII ends of the purified linear plasmid, which enables recircularisation to take place and generates plasmid pTG155 (C in FIG. 2).

The 8th amino acid of the mature glycoprotein (not possessing the signal sequence) of rabies virus strains ERA and CVS is proline, while in the cDNA isolated by Anilionis et al. there is found, in this position, a triplet coding for leucine.

In pTG155 shown in FIG. 3, the mutant site is flanked by an upstream EcoRI site in the vector and by a HindIII site on the sequences corresponding to amino acids 10 and 11 of the sequence coding for the mature glycoprotein. This small EcoRI-HindIII fragment is cloned in bacteriophage M13tg131(Kieny et al., 1983) in reverse orientation. Localised mutagenesis directed by an oligonucleotide is carried out according to the technique of Zoller and Smith (1983), using the oligonucleotide (5'-dATCACG-ATCCCAGACAAGC-3') synthesised as mentioned above.

The codon for amino acid 8 in the cDNA sequence is changed to replace CTA by CCA.

The oligonucleotide (19-mer) contains two modifications relative to the original sequence: a T in place of C, which corrects the triplet of leucine CTA to proline CCA, and an A in place of C which corresponds to a transversion in the GATA sequence. This generates a dam methylation sequence GATC which promotes the incorporation of the oligonucleotide sequence by correcting selective false pairings in vivo.

It should be noted that the EcoRI/HindIII fragment has been cloned in reverse orientation to that shown here so that the lower strand, complementary to the oligonucleotide, would be present in the single stranded M13 recombinant bacteriophage.

Areas of phage are examined for hybridisation under suitable conditions with the oligonucleotide labelled at its 5' end with $^{32}$p. A number of positive areas are withdrawn and the corresponding inserts are sequenced. The insert of one of the correctly modified clones is recloned in pTG155, exchanging the EcoRI/HindIII fragments to generate finally the restructured plasmid pTG155-pro. Analysis of the clones appearing during this stage is facilitated by the existence of a new site for the restriction enzyme Sau3A, which coincides with the dam methylation sequence introduced during the oligonucleotide-directed mutagenesis.

In plasmid pTG155-pro, the restructured rabies glycoprotein cDNA is flanked at each end by BglII sites. At the downstream end, the BGlII site originates from the use of the BglII-PstI adaptor oligonucleotide octamer used for cloning the PstI-PstI cDNA fragment in the BglII site, and the upstream site results from the use of a small double-stranded oligonucleotide designed to remove the G/C end.

Construction of Hybrid Plasmids

The combined sizes of the different elements needed for transfer of the sequence coding for the rabies glycoprotein into the VV genome, and the subsequent expression thereof, are of the order of several kb. It has hence been deemed necessary to minimise the size of the replication plasmid in E. coli used for the construction work, so as to facilitate the necessary manipulations.

The HindIII (Hin-J) fragment of thee VV genome contains the complete thymidine kinase (TK) gene which has already been used previously to permit the exchange and recombination of DNA inserted in the VV genome (Mackett et al., 1982). It is important to note that the transfer of an insert in the TK gene into the VV genome creates a TK-deficient virus which can be recognised by simple selection.

In the first place, it was necessary to produce a small sized plasmid bearing a single HindIII site which could be used for integration of the VV Hin-J fragment. Moreover, it was necessary to remove the unnecessary restriction sequences of the plasmid so as to enable the following manipulations to be performed.

The construction was primed starting from plasmid pML2 (Lusky and Botchan, 1981), which is a vector derived from plasmid pBR322 by spontaneous deletion in which the segment between nucleotide 1089 and 2491 has been lost (FIG. 4). The PstI sequence was first removed by inserting the AhaIII-AhaIII fragment of pUC8 (Vieira and Messing, 1982) between two AhaIII sites of pML2, removing 19 base pairs. The "linker-tailing" method (Lathe et al., 1984) was used to insert a HindIII linker, treated with S1, between the NruI and EcoRI sites of this plasmid, removing the BamHI site. This leads to a plasmid of 2049 base pairs carrying the functional β-lactamase gene (which confers resistance to ampicillin) and containing in addition an origin of replication active in E. coli and a single HindIII restriction site.

This construction has been called pTG1H.

The Hin-J fragment of the VV DNA carrying the TK gene has previously been cloned in a vector originating from pBR327 (Drillien and Spehner, 1983). This 4.6 kb fragment was recloned in the HindIII site of pTG1H. A clone was selected in which the TK gene is situated distally relative to the gene coding for ampicillin resistance.

This pTG1H-TK construction was used as a carrier in the following experiment.

The following stage was to isolate a VV promoter which could be used to control the expression of the sequence coding for the inserted rabies glycoprotein. The promoter of an early gene coding for a 7,500-dalton (7.5 K) protein has already been used successfully for an identical purpose (Smith et al., 1983), so this segment was isolated.

The 7.5 K gene is located on one of the smallest SaLI fragments (Gal-S fragment) of the VV type WR genome (Venkatasan et al., 1981). Since small fragments are cloned preferentially, a large proportion of the clones obtained by direct cloning of the VV type WR DNA cut with SalI in plasmid pBR322 carries the Sal-S fragment. This fragment is transferred to the vector bacteriophage M13mp701 (Kieny et al., 1983) by SalI digestion and religation, thereby leading to phage M13thSal-S.

In this clone, there is an ScaI site in immediate proximity to the initiation ATG of the 7.5 K gene. Down-stream of the 7.5 K gene, there are located single BamHI and EcoRI sites originating from the vector. The BamHI and ScaI sites are fused by way of a BglII linker 5'-CAGATCTG-3' by the "linker" technique, after completing the ends generated by BamHI digestion with the Klenow fragment of polymerase. This process removes the ScaI site but reconstitutes the BamHI site and shifts the single EcoRI site downstream. At the same time, the SalI(AccI) site downstream is removed, and the upstream site hence becomes unique.

This construction is called M13tg7.5K.

Within the Hind-J fragment of the VV DNA there are located ClaI and EcoRI sites which are separated by approximately 30 base pairs (Weir and Moss, 1983). The 7.5 K promoter fragment present in M13tg7.5K is excised with AccI and EcoRI and cloned between the ClaI and EcoRI sites of pTG1H-TK to generate pTG1H-TK-P7.5K, the synthesis of which is shown schematically in FIG. 5.

This construction leads to the transfer of the single BamHI site of the M13 vector immediately downstream of the 7.5 K promoter sequence. This single BamHI site is used in the following constructions.

pTG1H-TK-P7.5K is digested with BamHI and ligated with PTG155-pro digested with BglII (FIG. 5).

After transformation of E. coli, one of the recombinant plasmids isolated by this procedure, pVVgRAB, is selected, since it carries the cDNA of the rabies glycoprotein in the correct orientation for expression starting from the 7.5 K promoter.

pVVgRAB will sometimes be referred to as pTG1H-TK-P7.5K-gRAB.

Cloning in Vaccinia Virus (FIG. 6).

The strategy described by Smith et al. (1983) rests on the exchange in vivo between a plasmid carrying an insert into the VV TK gene and the wild-type viral genome, so as to inactivate the TK gene carried by the virus. The TK$^-$ viruses can be selected by spreading on a TK-negative cell line in the presence of 5-bromodeoxyuridine (5BUdR) (Mackett et al., 1982). Thymidine kinase phosphorylates 5BUdR to 5'-monophosphate, which is then converted to triphosphate. This compound is a dTTP analog and its incorporation in DNA blocks the correct development of the virus. A TK$^-$ virus can nevertheless replicate its DNA normally and leads to visible plaques in a similarly TK$^-$ cell layer.

Vaccinia virus propagates in the cytoplasm of infected cells rather than in their nucleus. For this reason it is not possible to take advantage of the host machinery of DNA replication and transcription, and the virion has to possess the components for expression of the viral gene. Purified VV DNA is non-infectious.

In order to generate recombinants, it is necessary to carry out simultaneously cell infection with a VV and transfection with the cloned DNA segment which is of interest Nevertheless, generation of the recombinants is limited to a small proportion of the cells which are competent for transfection with DNA. For this reason, it was necessary to implement an indirect "congruence" strategy to reduce the background of non-recombinant parent virus. This was accomplished by using as live infectious virus a temperature-sensitive mutant (ts) of vaccinia which is not capable of propagation at a non-permissive temperature of 39.5° C. (Drillien and Spehner, 1983). When cells are infected with a ts mutant under non-permissive conditions and transfected with DNA of a wild-type virus, viral multiplication will occur only in the cells which are competent for transfection and in which recombination between the wild-type viral DNA and the genome of the ts virus has taken place; there will be no outcome in the other cells despite their having been infected. If a recombinant plasmid containing a vaccinia DNA fragment such as pVVgRAB is included in the transfection mixture at the appropriate concentration with the wild-type DNA, it is also possible to procure its participation in the homologous recombination with the vaccinia DNA in the competent cells.

Primary cell monolayers of chick embyro fibroblasts (CEF) are infected at 33° C. with VV-Copenhagen ts 26 (0.1 pfu/cell) and transfected with a calcium phosphate coprecipitate of VV-Copenhagen wild-type DNA (0.5 $\mu$g/$10^6$ cells) and recombinant plasmid pTG1H-TK-P7.5K-gRAB (3.0 $\mu$g/$10^6$ cells). It should be noted that, in the following experiments, the lower concentrations (0.1 $\mu$g/$10^6$ cells) gave substantially improved yields of recombinants.

After incubation for 2 hours at a temperature which does not permit development of the ts virus (39.5° C.), the cells are rinsed and incubated for 48 hours at 39.5° C. Dilutions of ts$^+$ virus are used to reinfect an L-TK$^-$ mouse cell monolayer at 37° C., and are incubated in the presence of 5BUdR (100 $\mu$g/ml). Various TK$^-$ plaques are obtained from these cells which have received the recombinant plasmid, while control cultures without plasmids do not show visible plaques.

Correct reciprocal double recombination between the hybrid rabies/vaccinia plasmid and the VV genome exchanges the TK viral gene for the TK gene carried by the insert present in the plasmid. In the VV genome, the TK gene is present on a single HindIII:Hin-J fragment. The recombinants which have transferred the expression block of the rabies glycoprotein are presumed to have integrated an internal HindIII site derived from the glycoprotein cDNA. For this reason the purified DNA from TK$^-$ virus is digested with HindIII and subjected to agarose gel electrophoresis. As was predictable, the 4.6 kb Hin-J fragment is absent, and on the other hand two new 1.1 and 5.5 kb fragments reveal the presence of an insert containing an internal HindIII site. After sub-cloning of the TK$^-$ viruses, one of the recombinants, VVgRAB-26D3, is preserved.

Expression of the Rabies Glycoorotein starting from Recombinant Vaccinia Viruses.

Semi-confluent L-TK$^-$ cell monolayers are infected with VVgRAB-26D3 (50 pfu/cell) for 1 hour at room temperature, a methionine-free culture medium is then added, and after 30 min each culture dish is supplemented with [$^{35}$S]-l-methionine (1265 Ci/mmole) and incubation is continued at 37° C. for 4 hours. Cells are harvested, resuspended in an immunoprecipitation buffer containing protease inhibitors and, after ultrasonic rupture and clarification, the proteins bound by the anti-rabies antiserum are recovered by affinity chromatography on a protein A-sepharose resin, loaded on an electrophoresis gel and fluorgraphed by a techique described by Lathe et al., (1980).

Figure 7:
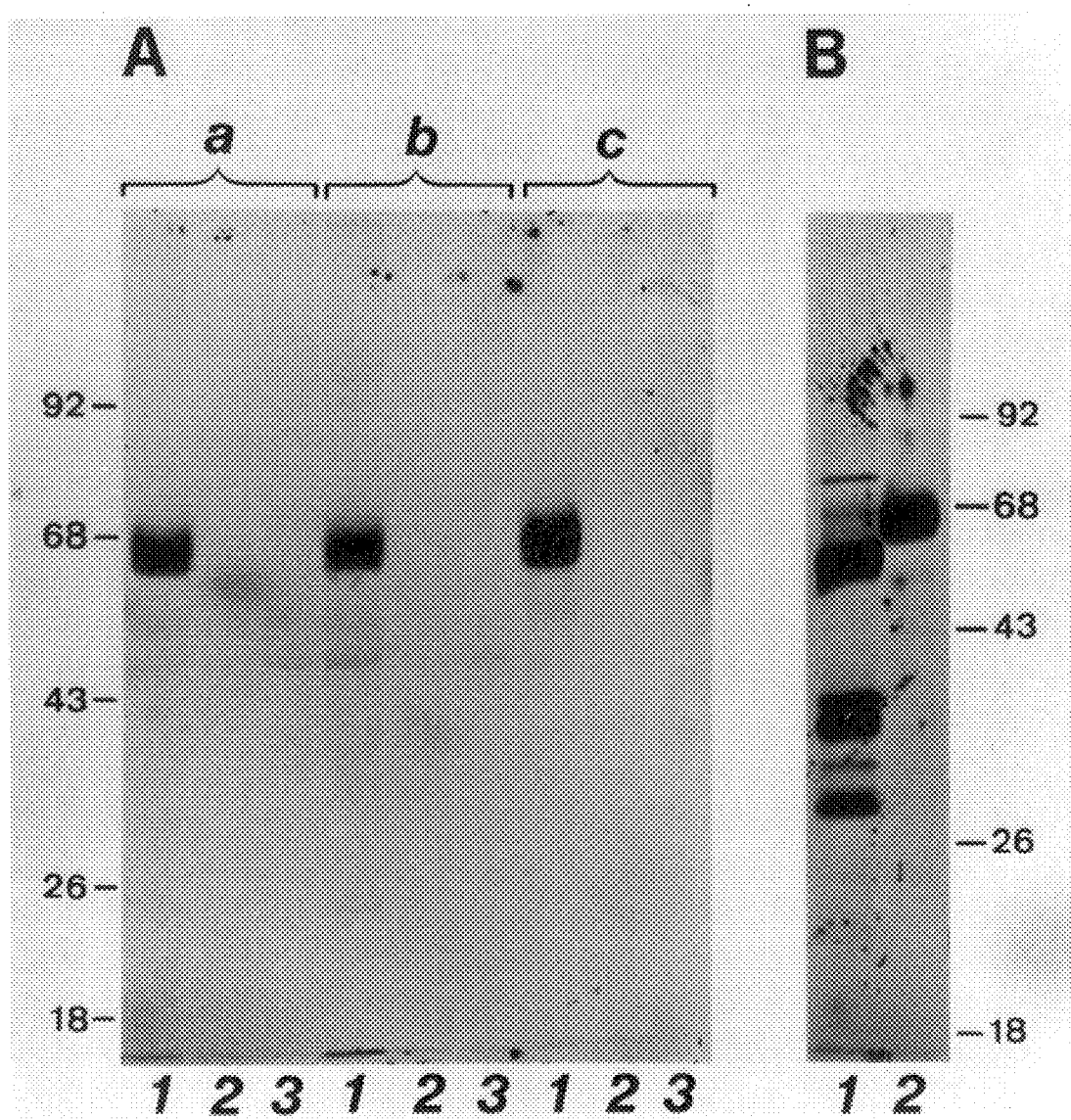
FIGS. 7A and 7B show an electrophoresis gel of protein extracted from a cell monolayer. In A the cell monolayer is infected with (1) the VVgRAB-26D3 recombinant, (2) the wild-type vaccinia virus, and (3) no virus. In B the cell monolayer is infected with VVgRAB-26D3 (1) in the presence or (2) in the absence of tunicamysin in the medium.

A polyclonal antiserum 3554-R215 prepared against the purified glycoprotein at the Wistar Institute was used in the experiments illustrated in FIG. 7, A (a) and 8; identical results are obtained (b,c) with two monoclonal antibodies neutralising the viruses (Wistar 509-6 and 101-1) which identify different epitopes on the rabies glycoprotein. In A the cell monolayer is infected with:

1) the VVgRAB-26D3 recombinant,
2) the wild-type vaccinia virus,
3) no virus.

In 8 a cell monolayer is infected with VVgRAB-26D3 and labelled in the presence (1) or absence (2) of tunicamycine (2 $\mu$g/ml).

In A and B the standard molecular weights are given in kilodaltons.

As is seen in FIG. 7A, a polyclonal rabies anti-serum, and likewise two monoclonal antibodies neutralising the virus, precipitate a protein which migrates in the form of a diffuse band with an apparent molecular weight of approximatey 66,000 daltons. This molecular weight corresponds exactly to the weight, 67,000 daltons, of an authentic rabies glycoprotein.

Since the molecular weight of the natural glycoprotein and the recombinant correspond, it was verified that the recombinant glycoprotein was glycosylated in vivo. A cell monolayer was infected with VVgRAB-26D3 as above, and to the medium there was added, before the labelling, a powerful inhibitor of glycosylation, tunicamycin (2 $\mu$g/ml). The infected cell extracts are immunoprecipitated using a polyclonal antibody and the product is loaded on an electrophoresis gel as above. As shown in FIG. 7B, the addition of tunicamycin to the medium leads to a reduction in the molecular weight of the 66,000-dalton recombinant glycoprotein, which corresponds to the removal of the glycosylated groups of the protein. It may hence be concluded from this that the recombinant rabies glycoprotein is glycosylated in the cells infected with VVgRAB. Various additional bands in lane (1) are presumed to be degradation products of the non-glycosylated rabies antigen.

In another experiment, an L-TK$^-$ cell monolayer is infected with VVgRAB-26D3 ($10^5$ pfu per plaque containing $10^6$ cells) and incubated for 8 hours at 37° C. The cells are fixed, and treated with monoclonal and polyclonal antibodies and, after very thorough washing, the bound antibody is detected using a second antibody (goat anti-mouse) labelled with fluorescein. The majority of the cells infected with the VVgRAB-26D3 recombinant (A) show significant fluorescence, whereas uninfected cells (C) and cells infected with non-recombinant viruses (B) do not show fluorescence.

As is brought out by FIG. 8, the fluorescence is associated predominantly with the cytoplasmic membrane, as could be expected of a transmembrane protein.

Immunological properties in vivo of the live hybrid vaccinia/rabies virus

Rabbits are immunised intradermally with $3 \times 10^7$ pfu of VVgRAB-26D3, and samples of serum are withdrawn after 0, 11 and 14 days. A recognisable swelling is observed at the site of infection which decreases after 8 to 9 days. An ERA rabies virus strain inactivated with β-propiolactone is labelled with $^{125}$I according to the standard protocol and tested for its reaction with the serum of the immunised animals.

The bound proteins are placed on electrophoresis gel and autoradiographed.

The 11- and 14-day sera, but not the serum of control day 0, were found to recognise and effectively bind the radiolabelled viral glycoprotein. The serum of control animals immunised with Copenhagen type non-recombinant vaccinia virus does not show such reactions. The serum of the immunised animals described above is then tested for inactivation of rabies viruses in vitro. The dilutions of rabies strain ERA are preincubated for 1 hour with different amounts of the rabbit antiserum, and plated on new born hamster kidney (BHK) cells on microtitration plates ($10^3$ cells/well). After incubation at 37° C. for 22 hours, the productive infected cells are stained using a direct immunofluorescence technique.

Table I shows that, even at the greatest dilutions of the 11- and 14-day antiserum, complete inactivation of the virus is obtained. The preimmune and non-recombinant sera do not give detectable neutralisation. The titres are given as the greatest dilution at which inhibition of infection is observed.

TABLE 1

| No. of days after vaccination | VVgRAB26D3 | | | | Wild-type vaccinia |
|---|---|---|---|---|---|
| | Rabbit I | Rabbit II | Rabbit III | Rabbit IV | |
| 0 | 0 | 0 | 0 | 0 | 0 |
| 11 | 10,000 | 10,000 | 10,000 | 10,000 | 0 |
| 14 | >30,000 | >30,000 | >30,000 | >30,000 | 0 |

These results show that, not only does the VVgRAB-26D3 recombinant induce production of antibodies which react with rabies virus, but also that the antiserum of immunised animals is capable of inactivating rabies virus in vitro. The induction of neutralising antibodies does not always corollate with protection against the development of the disease. For this reason, a direct study has been carried out of a test of protection using the recombinant virus. Mice are immunised by injection in the leg or by scratching the tail with $10^7$ pfu of live VVgRAB-26D3. These animals are then inoculated with a lethal dose (1,000 $LD_{50}$ units) of a wild-type rabies virus introduced by intracerebral injection. After 10 days, the group of control animals immunised with non-recombinant vaccinia show terminal rabid infection, which in contrast 15 out 15 animals immunised with VVgRAB-26D3 show no trace of disease.

It may therefore be concluded that immunisation with the live vaccinia/rabies recombinant virus leads to protection against rabies.

Immunological Properties in vivo of the Inactivated Hybrid Vaccinia/Rabies Virus Three types of inactivated vaccine can be prepared from cells infected with vaccinia/rabies recombinant virus: either a crude extract of infected cells, or purified intact virus, or purified glycoprotein G. The three preparations are inactivated with β-propiolactone.

BHK cells infected with VVgRAB-26D3 are homogenised in a Dounce grinder and the centrifugation supernatant represents the crude cell extract.

To obtain the killed purified virus, this preparation is inactivated with 1/4,000 β-propiolactone and centrifuged on a sucrose gradient according to conventional techniques.

The purified glycoprotein G is obtained by solubilisation of the crude extract in the presence of 2% strength Triton x-100. After centrifugation for 1 hour at 100,000 g, G is isolated from the supernatant by passage on an affinity column prepared with a monoclonal anti-G antibody. This purified glycoprotein G is also inactivated with β-propiolactone.

Mice are immunised with two intraperitoneal injections of 0.5 ml of these inactivated preparations at an interval of 1 week, and subjected to the test 1 week later (240 $LD_{50}$ units) by the intracerebral route.

Table II shows the anti-rabies antibodies measured on days 7 and 14.

TABLE II

| | Amount of injected protein in μg/mouse | Titre of anti-rabies antibodies | |
|---|---|---|---|
| | | Day 7 | Day 14 |
| VVgRAB-26D3 crude extract | 140 | 80 | 8,000 |
| VVgRAB-26D3 purified virus | 9 | 270 | 4,000 |
| VVgRAB-26D3 purified G | 50 | 120 | 15,000 |
| Copenhagen type vaccinia crude extract | 900 | 10 | 10 |

All the animals vaccinated with the different preparations of inactivated vaccine derived from VVgRAB-26D3 survive the intracerebral injection of rabies virus, whereas the animals of the control group die at the expected time.

It is important to note that, even when inactivated, the hybrid VVgRAB-26D3 virus confers effective protection against experimental rabies infection. This shows that, in the intact recombinant virus, the rabies glycoprotein is presented at the surface of the virion and is capable of inducing an immunological response similar to that induced by inactivated rabies virus.

Vaccination of Foxes and Vaccination by the Oral Route

In Western Europe, the fox is the main agent of dissemination of rabies. It is therefore of basic importance to be able to control the vaccination of foxes. This will preferably be carried out by the oral route in order to minimise handling of the animals.

Red foxes (*Vulpes vulpes*) less than one year old are immunised by various routes with $10^8$ pfu of live VVgRAB-26D3. The controls consist of two foxes vaccinated with classical killed anti-rabies vaccine and 4 foxes vaccinated with wild-type vaccinia.

Table III gives the anti-rabies antibody titre measured on days 7, 14 and 28. This table shows that, in foxes as in mice, the vaccinia/rabies recombinant virus induces production of antibodies comparable to that induced by the classical vaccine.

Vaccinated animals are subjected to the test of injection of virulent rabies virus on day 28.

The foxes vaccinated with wild-type virus die a⁺ the expected time. All the foxes vaccinated with the classical killed vaccine or with VVgRAB-26D3 [even the fox (2) inoculated subcutaneously which had no serum-neutralsing antibodies] are alive 2 months after the test.

| Vaccine used | Inoculation route | | Antibody titre* | | |
|---|---|---|---|---|---|
| | | | Day 6 | Day 14 | Day 18 |
| Killed classical | Subcutaneous | (1) | 0.33 | 0.64 | 0.24 |
| | | (2) | 0.07 | 0.05 | 0.07 |
| Wild-type vaccinia | Intradermal | | — | — | — |
| VVgRAB-26D3 | Intradermal | (1) | 0.64 | 6.1 | 4.4 |
| | | (2) | 0.05 | 0.6 | 1.67 |
| VVgRAB-26D3 | Subcutaneous | (1) | 0.46 | 2.32 | 4.3 |
| | | (2) | — | — | — |
| VVgRAB-26D3 | Oral with scarification of the mucosa | (1) | 0.33 | 0.88 | 1.67 |
| | | (2) | 0.24 | 0.88 | 2.31 |

*The antibody titres are expressed in international units (reference serum - 65 I.U. - neutralising at $10^{-4.2}$)

The following strain has been filed in the Collection Nationale de Cultures de Microorganismes (CNCM)

(National Collection of Microorganism Cultures) –28, rue de Docteur Roux, 75724 PARIS CEDEX 15: *E. coli* TGE1106 transformed by pTG171 No. I-248 filed on Sep. 30, 1983.

REFERENCES

Anilionis, A., Wunner, W. H. & Curtis, p.J. (1981) Nature 294, 275–278.

Drillien, R. & Spehner, D. (1983) Virology 131, 385–393.

Kieny, M. P., Lathe, R. & Lecocq, J. P. (1983) Gene 26, 91–99.

Kohli, V., Balland, A., Wintzerith, M., Sauerwald, R.,

Staub, A. & Lecocq, J. P. (1982) Nucleic Acids Res. 10, 7439–7448.

Kozak, M. (1981) Nucleic Acid Res. 9, 5233–5252.

Kozak, M. (1983) Microbiol. Rev. 47, 1–45.

Lathe, R., Hirth, P., Dewilde, M., Harford, N. & Lecocq, J. P. (1980) Nature 284, 473–474.

Lathe, R., Balland, A., Kohli, V. & Lecocq, J. P. (1982) Gene 20, 187–195.

Lathe, R., Kieny, M. P., Schmitt D., Curtis, P. & Lecocq, J. P. (1984a) J. Mol. Appl. Genet., in press.

Lathe, R., Kieny, M. P., Skory, S. & Lecocq, J. P. (1984a) DNA, in press.

Lusky, M., Botchan, M. (1981) Nature 293, 79–81.

Mackett, M., Smith, J. L. & Moss, B., (1982) Proc. Natl. Acad. Sci. USA 79, 7415–7419.

Panicali, D. & Paoletti, E. (1982), Proc. Natl. Acad. Sci. USA 79, 4927–4931. Panicali, D., Davis, S. W., Weinberg, R. L. & Paoletti, E. (1983) Proc. Natl. Acad. Sci. USA 80, 5364–5368.

Smith, G. L., Mackett, M. & Moss, V. (1983) Nature 302, 490–495.

Soberon et al., Gene 9, 287–305 (1980).

Venkatesan, S., Baroudy, B. M. & Moss, B. (1981) Cell 125, 805–813.

Vieira, J. & Messing, J. (1982) Gene 19, 259–268.

Weir, J. P. & Moss, B. (1983) J. Virol. 46, 530–537.

Wiktor, T. J. (1978) Develop. Biol. Standard 40, 255–264.

Wiktor, T. J. (1980) in *Rhabdoviruses* III pp. 99–112 (ed. D. H. L. Bishop) CRC Press, Inc.

Wunner, W. H., Dietzschold, B., Curtis, P. J. & Wiktor, T. J. (1983) J. Gen. Virol. 64, 1649–1659.

Yelverton, E., Norton, S., Obijeski, J. F. & Doeddel, D. V. (1983) Science 219, 614–620.

Zoller, M. J. & Smith, M. (1983) in *Methods in Enzymology*, Vol. 100, pp. 468–500 (Eds. Wu, R., Grossman, L., Moldave, K.) Academic Press, London.

Keller F., Drillien R. and Kirn A.: Thermosensibilite du developpement des poxvirus et virulence. Utilisation de souches thermosensibles comme vaccin. Rencontre Biologique, 1978 (L. Hartmann), p. 121–126, Ed. Varia, Paris.

Keller F. and Drillien R.: Un mutant thermosensible attenue du virus vaccinal. Ann. Virol. (INSTITUT PASTEUR), 1980, 131 E, 85–94.

We claim:

1. A hybrid vaccinia virus containing a DNA sequence encoding the amino acid sequence of rabies glycoprotein G inserted in a vaccinia thymidine kinase gene under the control of the 7.5 K vaccinia virus promoter.

2. The hybrid vaccinia according to claim 1 wherein said rabies glycoprotein G has the following first 8 N-terminal amino acids in the mature protein:

Lys Phe Pro Ile Tyr Thr Ile Pro.

3. The hybrid vaccinia virus according to claim 1 wherein said DNA sequence is present in a non-essential segment of vaccinia virus.

4. The hybrid vaccinia virus according to claim 1 wherein said virus is temperature sensitive.

5. A vaccine for preventing and treating rabies comprising a hybrid vaccinia virus containing a DNA sequence encoding the amino acid sequence of rabies glycoprotein G inserted in a vaccinia thymidine kinase gene under the control of the 7.5 K vaccinia virus promoter, and a pharmaceutically acceptable carrier.

6. The vaccine according to claim 5 wherein said hybrid vaccinia virus is live.

7. A method of preventing rabies in a mammal comprising administering to said mammal a hybrid vaccinia virus containing a DNA sequence encoding rabies glycoprotein G inserted in a vaccinia thymidine kinase gene under the control of the 7.5 K vaccinia virus promoter, in an amount sufficient to prevent rabies.

8. A recombinant vaccinia virus containing a DNA sequence present in a non-essential segment of vaccinia virus, encoding the amino acid sequence of rabies glycoprotein G as depicted in FIGS. 1*a–b* starting from Lysine residue in position 1 and replacing the Leucine residue in position 8 with a Proline residue, wherein said DNA sequence is inserted in a vaccinia thymidine kinase gene under the control of the 7.5 K vaccinia virus promoter placed upstream of the DNA sequence.

9. A recombinant vaccinia virus according to claim 8, wherein the said amino acid sequence is preceded by a signal sequence as depicted in FIGS. 1*a–b*, from position −19 to −1.

* * * * *